(12) United States Patent
Springer

(10) Patent No.: US 6,680,395 B2
(45) Date of Patent: Jan. 20, 2004

(54) METHOD FOR THE SYNTHESIS OF STRAIGHT-CHAIN ALIPHATIC CARBOXYLIC ACIDS FROM ALDEHYDES

(75) Inventor: Helmut Springer, Dinslaken (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/204,495

(22) PCT Filed: Feb. 21, 2001

(86) PCT No.: PCT/EP01/01940

§ 371 (c)(1),
(2), (4) Date: Sep. 5, 2002

(87) PCT Pub. No.: WO01/66503

PCT Pub. Date: Sep. 13, 2001

(65) Prior Publication Data

US 2003/0100781 A1 May 29, 2003

(30) Foreign Application Priority Data

Mar. 4, 2000 (DE) .......................... 100 10 770

(51) Int. Cl.$^7$ .............................. C07C 51/16
(52) U.S. Cl. ................ 554/134; 554/132; 560/523; 560/531
(58) Field of Search ................ 554/132, 134; 560/523, 531

(56) References Cited

FOREIGN PATENT DOCUMENTS

| DE | 1083800 | | 6/1960 |
| DE | 1154454 | * | 9/1963 |

* cited by examiner

*Primary Examiner*—Deborah Carr
(74) *Attorney, Agent, or Firm*—Muserlian, Lucas and Mercanti

(57) ABSTRACT

The invention relates to a non-catalysed method for the synthesis of straight-chain aliphatic carboxylic acids by oxidation of straight-chain aldehydes with oxygen-containing gas mixtures. The invention is characterised in that during the novel process of oxidation branched aldehydes are present in the reaction mixture.

13 Claims, No Drawings

METHOD FOR THE SYNTHESIS OF STRAIGHT-CHAIN ALIPHATIC CARBOXYLIC ACIDS FROM ALDEHYDES

This application is a 371 of PCT/EP01/01940 filed Feb. 21, 2001.

The present invention relates to a novel, noncatalytic process for preparing straight-chain aliphatic carboxylic acids from aldehydes by oxidation with oxygen or oxygen-containing gas mixtures.

Aldehydes are used on a large scale as starting materials for obtaining carboxylic acids. The preference for aldehydes for this area of use derives from their ready availability by a number of processes, which are also used in industry. Moreover, the carbonyl of the aldehydes can easily be converted into the carboxyl group characteristic of carboxylic acids. In processes applied industrially, the conversion of aldehydes to carboxylic acids mainly takes place in the presence of catalysts. However, processes in which the use of catalysts is dispensed with are also known. To avoid side reactions, both the catalytic and the noncatalytic/processes employ temperatures which are as low as possible, and in general the reaction temperature does not exceed 100° C. Suitable catalysts are mainly salts of transition metals, in particular salts of cobalt and of manganese, and of chromium, iron, copper, nickel, silver and vanadium. The formation of carboxylic acids from aldehydes is frequently associated, even if optimal temperature conditions are maintained, with side reactions and degradation reactions. This applies equally to reactions in the presence and in the absence of catalysts. In such cases, the selectivity of the conversion can be considerably improved by adding alkali metal salts of weak acids to the reactants. However, the disadvantage of this variant of the process is that the salts have an inhibitory effect, so that long reaction times are necessary for complete conversion of the starting materials.

In the process described in DE-A 30 29 700, the appropriate aldehydes for preparing aliphatic monocarboxylic acids having 6 to 9 carbon atoms are oxidized with oxygen in pure form or with air. A combination of manganese and copper compounds which are soluble in the acid acts as catalyst, the molar ratio of manganese to copper being in the range from 5:1 to 0.5:1. The conversion of the starting materials takes place in liquid phase at temperatures of about 50 to 80° C. and pressures in the range from about 1.4 to 10.3 bar. The main difficulty of this process is described, in the description of the process, as being the presence of copper compounds, and manganese compounds, in the reaction product, i.e. in the carboxylic acid. Elaborate purification measures are necessary to remove the metals, for example precipitation thereof with aqueous oxalic acid.

The process disclosed in U.S. Pat. No. 4,487,720 for preparing $C_5$ to $C_9$ monocarboxylic acids by oxidizing aldehydes with the same number of carbon atoms using pure oxygen or air likewise operates with copper and manganese compounds as catalysts. The disadvantage described for this procedure is the formation of copper films which appear on purification of the acid by distillation and result in mechanical damage to the distillation apparatus. To avoid this problem, it is recommended that the distillation be carried out in the presence of oxygen.

Another catalytic process for reacting aldehydes with oxygen to form carboxylic acids is disclosed in the published international application WO 97/14668. The catalysts used are substituted or unsubstituted alkylamines, alkylamine N-oxides, aromatic amines, aromatic N-oxides, heterocyclic amines, heterocyclic amine N-oxides and mixtures thereof. It is expressly pointed out that the nitrogen compounds with catalytic activity must have a higher boiling point than the product of the reaction in order to suppress contamination of the acid by the catalyst.

According to the teaching of the published Japanese patent application 53-105413, α-branched aliphatic aldehydes are oxidized with oxygen in the presence of lithium or alkaline earth metal compounds, which are employed in amounts of from 0.01 to 10% by weight (based on the complete reaction system), in order to prepare α-branched aliphatic carboxylic acids.

The procedure described in the French patent application 2 769 624 is characterized by maintaining low reaction temperatures, namely temperatures between 0 and 25° C. The process likewise requires the presence of alkali metal or alkaline earth metal compounds as auxiliaries. It is not disclosed what specific effects these compounds display, i.e. whether they merely improve the selectivity of the conversion, as known, or else possibly also increase the rate of reaction at the chosen low temperatures.

Mixtures of isomeric branched aliphatic or cycloaliphatic carboxylic acids are obtained by the procedure of German patent 1 154 454 from aldehydes which are oxidized in a thin liquid layer at a temperature of 65 to 110° C. with an oxygen-containing gas without use of catalysts. The reaction is carried out in tubes which are empty or packed with inert materials with a large surface area. The proportion of acid in the product of the reaction is between 59 and 80%.

The starting material employed in all the known oxidation processes for preparing carboxylic acids comprises structurally homogeneous aldehydes, i.e. either straight-chain or branched compounds of the same molecular size (number of carbon atoms). An important reason for the use of substantially pure carbonyl compounds for further processing is the attempt to avoid additional process steps in the form of separation operations. An additional aim is to preclude constituents having a disruptive effect, which put a strain on the oxidation process and/or impair the quality of the product of the reaction.

Accordingly, a large number of processes are known for fractionating mixtures of isomeric aldehydes, which may also contain other constituents, for example catalysts, secondary products of aldehydes, such as alcohols, acids and condensation products, into the pure components. A procedure which is frequently used but is not without problems, because of the thermal sensitivity of aldehydes, is distillation. In order to put as little stress as possible on the aldehydes, therefore, it is expedient to connect a plurality of distillation columns in series and carry out the distillation with a residence time which is as short as possible. In some cases, separation and purification of the aldehydes are also possible by azeotropic distillation with water or other entrainers.

Aldehydes are often purified, especially in laboratory practice, via addition and condensation products which, after the separation step, are cleaved to form the aldehydes again. Examples of addition and condensation products of aldehydes are hydrazones, bisulfite adducts (cf. DE 24 59 152) and acetals.

Purification of higher n-alkanals from n/iso-aldehyde mixtures obtained by hydroformylation can take place by treating the aldehyde mixture with nonoxidizing acids. The 1,3,5-trioxanes of the straight-chain aldehydes resulting from this are removed by fractional crystallization (cf. DE 22 18 305).

The known processes for preparing carboxylic acids from aldehydes do not meet the requirements for modern processes used industrially, and not only because of the recommendation that alkanals of the same molecular size and structure should preferably be employed. In addition, the use of catalysts is also associated with elaborate purification steps, to which the product of the reaction must be subjected in order to obtain carboxylic acids which can be processed further without problems. Noncatalytic processes are frequently unsatisfactory in terms of the conversion and selectivity for the required product.

The object therefore was to develop a procedure which avoids the disadvantages mentioned and makes it possible to obtain carboxylic acids from aldehydes in high yield with acceptable technical complexity.

This object is achieved by a process for preparing straight-chain aliphatic carboxylic acids having 4 to 11 carbon atoms by oxidation of the corresponding straight-chain aldehydes with oxygen or oxygen-containing gas mixtures at 20 to 100°C. The process comprises carrying out the oxidation of the straight-chain aldehydes in the presence of from 1 to 30 mol % of branched aldehydes per mol of straight-chain aldehydes.

Surprisingly the addition of branched aldehydes to the reaction mixture makes it possible to carry out the oxidation of n-aldehydes to the corresponding carboxylic acids with pure oxygen or oxygen as constituent of gas mixtures, with high conversion, very selectively and without the use of catalysts.

The branched aldehydes added according to the invention to the oxidation mixture are preferably saturated and contain 3 to 15, in particular 4 to 11, carbon atoms in the molecule. Although the use of unsaturated branched aldehydes is not ruled out, it will be confined to exceptional cases. It must be taken into account in this connection that unsaturated compounds are more prone than saturated compounds to form oxygen-containing degradation products in an oxidizing milieu. Side reactions of this type are unwanted because they may lead to contamination of the n-carboxylic acids.

The term branched aldehydes means according to the current rules of nomenclature alkanals which, besides a main chain consisting of carbon atoms arranged in a row, also have one or more side chains containing carbon atoms. The location of these side chains in the molecule, the number thereof and the length thereof are subject to no restrictions. However, the aldehydes preferably employed will be, because of their easy accessibility, those whose side chain is located on the α or β carbon atoms (i.e. in position 2 or 3) in relation to the carbonyl group. The branched aldehyde normally contains only one side chain. If a plurality of side chains is present in the molecule, they may contain the same or different numbers of carbon atoms. Preferred side chains are the methyl and ethyl radicals. Examples of branched aldehydes are isobutyraldehyde, 2-methylbutanal, 3-methylbutanal (isovaleraldehyde), 2-methylpentanal, 2-methylhexanal, 2-ethylhexanal, 2-methyloctanal, 3,5,5-trimethylhexanal.

From 1 to 30 mol %, preferably 2 to 15 mol % and, in particular, 5 to 10 mol % of branched aldehyde are added per mol of unbranched aldehyde to the reaction mixture. Aldehydes with α and β branches have proved particularly suitable. Compared with these, aldehydes whose side chain is further away from the carbonyl group are less effective.

It is unnecessary for there to be agreement between straight-chain and branched aldehyde in molecular size. Nor is it necessary to employ branched aldehydes of uniform structure and/or molecular size. On the contrary, it is also possible to use mixtures of two or more different branched aldehydes. It is therefore possible not only for the branched aldehydes used for carrying out the oxidation reaction to be selected so that they can, in the form of the branched acids formed from them, be easily separated from the desired product, but also to take account of economic demands, for example availability and good value.

There have been no detailed investigations of the mode of action of the branched aldehydes in the oxidation process. To explain the reaction mechanism, it can be assumed that the concentration of initially produced carbon free radicals in the reaction mixture is crucial for the oxidation process. It is evident that such free radicals are produced more easily from branched aldehydes than from straight-chain aldehydes, with the consequence that free radicals are available in higher concentration in the presence of branched aldehydes in the reaction mixture than when exclusively unbranched aldehydes are present.

The branched aldehyde is normally added to the reaction mixture in an amount such that the required ratio of straight-chain to branched aldehyde is set up. Conversely, if an excess of branched aldehyde is present in the reaction mixture, it is possible either to add an appropriate amount of n-aldehyde or else to remove some of the branched aldehyde. Special cases in which the preparation process itself results in the aldehyde mixture required for the oxidation stage are, of course, also conceivable.

The process of the invention is carried out in the temperature range from 20 to 100° C. It is preferably carried out at between 20 and 80° C., in particular between 40 and 80° C. The temperature management, constant or variable temperature, can be adapted to the uniform structure and/or molecular size. On the contrary, it is also possible to use mixtures of two or more different branched aldehydes. It is therefore possible not only for the branched aldehydes used for carrying out the oxidation reaction to be selected so that they can, in the form of the branched acids formed from them, be easily separated from the desired product, but also to take account of economic demands, for example availability and good value.

There have been no detailed investigations of the mode of action of the branched aldehydes in the oxidation process. To explain the reaction mechanism, it can be assumed that the concentration of initially produced carbon free radicals in the reaction mixture is crucial for the oxidation process. It is evident that such free radicals are produced more easily from branched aldehydes than from straight-chain aldehydes, with the consequence that free radicals are available in higher concentration in the presence of branched aldehydes in the reaction mixture than when exclusively unbranched aldehydes are present.

The branched aldehyde is normally added to the reaction mixture in an amount such that the required ratio of straight-chain to branched aldehyde is set up. Conversely, if an excess of branched aldehyde is present in the reaction mixture, it is possible either to add an appropriate amount of n-aldehyde or else to remove some of the branched aldehyde. Special cases in which the preparation process itself results in the aldehyde mixture required for the oxidation stage are, of course, also conceivable.

The process of the invention is carried out in the temperature range from 20 to 100° C. It is preferably carried out at between 20 and 80° C., in particular between 40 and 80° C. The temperature management, constant or variable temperature, can be adapted to the individual requirements of the starting material and to the reaction circumstances.

The reactants are preferably reacted under atmospheric pressure. The use of elevated pressure is not, however, precluded. The working range is normally from atmospheric pressure to 1.0 MPa, preferably atmospheric pressure to 0.8 MPa.

The reaction time needed to convert aldehydes into carboxylic acids by the process of the invention depends inter alia on the reaction temperature, the nature of the starting materials and the ratio of the amounts of the reactants. It is normally from 30 min to 20 h, in particular 3 to 8 h.

The novel process is centered on the oxidation of unbranched $C_4$ to $C_{11}$ aldehydes. The origin of the aldehydes is not restricted to particular preparation processes. Aldehydes obtained by oxo process, i.e. by reacting $C_3$ to $C_{10}$ olefins with carbon monoxide and hydrogen, are preferred because of their ready availability. It is immaterial in this connection which specific embodiment of the oxo process was used to obtain the aldehydes, i.e. whether the reaction was catalyzed, for example, by cobalt or by rhodium, whether the metals were employed alone or together with complexing agents, and the catalyst was homogeneously dissolved in the reaction mixture or formed a separate heterogeneous phase.

The oxidizing agent used in the process of the invention is molecular oxygen or gas mixtures containing molecular oxygen. Other constituents of such gas mixtures are inert gases, for example nitrogen, noble gases and carbon dioxide. The proportion of inert constituents in the oxygen-containing gas mixture is up to 90% by volume, in particular 30 to 80% by volume. The preferred oxidizing agents are oxygen or air.

The aldehydes can be employed as such or dissolved in a solvent which is inert under the reaction conditions. Examples of suitable solvents are ketones such as acetone, esters, for example ethyl acetate, hydrocarbons, for example toluene, and nitrohydrocarbons such as nitrobenzene. The concentration of the aldehyde is limited by its solubility in the solvent.

The process of the invention can be carried out batchwise or continuously. Recycling of unreacted reactants is possible in both cases.

In a proven embodiment of the process of the invention, n-aldehyde and branched aldehyde are placed in a suitable reactor, for example a tubular reactor which is provided with a distributor plate and optionally also contains packings, and the oxygen or the oxygen-containing gas mixture is passed upwards through the aldehyde.

In another embodiment, the reactor used is a trickle tower containing packings. The aldehyde is allowed to trickle down over the packing and, at the same time, oxygen or an oxygen-containing gas mixture is passed cocurrently or countercurrently into the tower. Irrespective of the particular design of apparatus for the process of the invention, the required reaction product, i.e. the straight-chain aliphatic carboxylic acid, must be separated from the concomitant substances, in particular from the branched carboxylic acid formed from the branched aldehyde. The straight-chain acid is isolated from the reaction mixture by conventional processes. Those suitable are distillation under atmospheric or reduced pressure and carrier distillation, for example in the familiar embodiment of steam distillation. It is also possible to separate the main product from the inevitably produced concomitant substances by fractional crystallization. The separation operation to be used in the individual case depends on the individual possibilities and requirements. It is self-evident that the branched carboxylic acid formed from the branched aldehyde during the oxidation process can also be used further, directly or after chemical modification, as product of value.

The following examples describe the preparation of n-pentanoic acid, n-heptanoic acid and n-nonanoic acid by the process of the invention. The reaction of the appropriate starting aldehydes takes place in the presence of branched aldehydes as reaction auxiliaries. The examples are compared with the results of comparative tests in which the n-aldehyde was oxidized alone, i.e. in the absence of branched aldehyde. The results of the respective tests are indicated by stating the following characteristic variables:

weight of oxidation product (crude acid); it correlates with the conversion;

GC analysis of the crude acid; the forerun and after-run components are not subdivided but combined under the designations low boilers and high boilers;

aldehyde conversion; irrespective of the addition of a branched aldehyde to the reaction mixture, the aldehyde conversion relates exclusively to the straight-chain compound;

selectivity; this is derived from the amount of n-carboxylic acid in the reaction product relative to reacted n-aldehyde.

The novel process is, of course, not confined to the embodiments described hereinafter.

EXAMPLES

Preparation of N-Pentanoic Acid

Comparative Example 1

The liquid-phase oxidation of n-pentanal to n-pentanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 $\mu$m and was connected to the bubble column.

In each of the oxidations, 800.0 g of n-pentanal of the following composition determined by gas chromatography were employed:

0.17% low boilers 99.33% n-pentanal 0.42% n-pentanoic acid 0.08% high boilers

The results after oxidation at a constant 50° C. for 6 hours were as follows:

| Weight of oxidation product (g) | 932.9 |
|---|---|
| GC analysis (%): | |
| Low boilers | 0.44 |
| n-Pentanal | 3.56 |
| n-Pentanoic acid | 95.24 |
| High boilers | 0.76 |
| n-Pentanal conversion (% of theory) | 96.3 |
| Selectivity for n-pentanoic acid (% of theory) | 99.0 |

Example 1

This test was carried out under the conditions of comparative example 1 with the difference that the starting aldehyde contained 5.36% by weight methylbutanal in addition to 93.96% by weight n-pentanal (equivalent to a molar ratio of 100 to 5.70).

800.0 g of this mixture were employed in the oxidation.

The results after oxidation at a constant 50° C. for 6 hours were as follows:

| Weight of oxidation product (g) | 935.2 |
|---|---|
| GC analysis (%): | |
| Low boilers | 0.77 |
| 2-Methylbutanal | 0.06 |
| n-Pentanal | 2.75 |
| 2-Methylbutyric acid | 4.95 |
| n-Pentanoic acid | 91.02 |
| High boilers | 0.45 |
| n-Pentanal conversion (% of theory) | 97.00 |
| Selectivity for n-pentanoic acid (% of theory) | 99.40 |

Example 2

This test was carried out under the conditions of comparative example 1 with the difference that the starting aldehyde contained 10.48% by weight 2-methylbutanal in addition to 88.88% by weight n-pentanal (equivalent to a molar ratio of 100 to 11.79).

800.0 g of this mixture were employed in the oxidation.

The results after oxidation at a constant 50° C. for 6 hours were as follows:

| Weight of oxidation product (g) | 934.7 |
|---|---|
| GC analysis (%): | |
| Low boilers | 1.27 |
| 2-Methylbutanal | 0.15 |
| n-Pentanal | 2.14 |
| 2-Methylbutyric acid | 9.49 |
| n-Pentanoic acid | 86.39 |
| High boilers | 0.56 |
| n-Pentanal conversion (% of theory) | 97.5 |
| Selectivity for n-pentanoic acid (% of theory) | 99.3 |

Example 3

This test was carried out under the conditions of comparative example 1 with the difference that the starting aldehyde contained 20.33% by weight 2-methylbutanal in addition to 79.01% by weight n-pentanal (equivalent to a molar ratio of 100 to 25.73).

800.0 g of this mixture were employed in the oxidation.

The results after oxidation at a constant 50° C. for 6 hours were as follows:

| Weight of oxidation product (g) | 933.9 |
|---|---|
| GC analysis (%): | |
| Low boilers | 2.43 |
| 2-Methylbutanal | 0.25 |
| n-Pentanal | 1.85 |
| 2-Methylbutyric acid | 18.40 |
| n-Pentanoic acid | 76.45 |
| High boilers | 0.62 |
| n-Pentanal conversion (% of theory) | 97.6 |
| Selectivity for n-pentanoic acid (% of theory) | 99.0 |

Example 4

This test was carried out under the conditions of comparative example 1 with the difference that the starting aldehyde contained 5.31% by weight 3-methylbutanal in addition to 94.05% by weight n-pentanal (equivalent to a molar ratio of 100 to 5.64).

800.0 g of this mixture were employed in the oxidation.

The results after oxidation at a constant 50° C. for 6 hours were as follows:

| Weight of oxidation product (g) | 935.2 |
|---|---|
| GC analysis (%): | |
| Low boilers | 0.39 |
| 3-Methylbutanal | 0.20 |
| n-Pentanal | 2.67 |
| 3-Methylbutyric acid | 5.16 |
| n-Pentanoic acid | 91.16 |
| High boilers | 0.42 |
| n-Pentanal conversion (% of theory) | 97.1 |
| Selectivity for n-pentanoic acid (% of theory) | 99.3 |

Example 5

This test was carried out under the conditions of comparative example 1 with the difference that the starting aldehyde contained 10.05% by weight 3-methylbutanal in addition to 89.38% by weight n-pentanal (equivalent to a molar ratio of 100 to 11.31).

800.0 g of this mixture were employed in the oxidation.

The results after oxidation at a constant 50° C. for 6 hours were as follows:

| Weight of oxidation product (g) | 934.7 |
|---|---|
| GC analysis (%): | |
| Low boilers | 0.40 |
| 3-Methylbutanal | 0.38 |
| n-Pentanal | 2.39 |
| 3-Methylbutyric acid | 9.71 |
| n-Pentanoic acid | 86.70 |
| High boilers | 0.42 |
| n-Pentanal conversion (% of theory) | 97.3 |
| Selectivity for n-pentanoic acid (% of theory) | 99.4 |

Example 6

This test was carried out under the conditions of comparative example 1 with the difference that the starting aldehyde contained 20.04% by weight 3-methylbutanal in addition to 79.32% by weight n-pentanal (equivalent to a molar ratio of 100 to 25.26).

800.0 g of this mixture were employed in the oxidation.

The results after oxidation at a constant 50° C. for 6 hours were as follows:

| Weight of oxidation product (g) | 934.4 |
|---|---|
| GC analysis (%): | |
| Low boilers | 0.36 |
| 3-Methylbutanal | 0.67 |
| n-Pentanal | 1.80 |
| 3-Methylbutyric acid | 19.52 |
| n-Pentanoic acid | 77.30 |
| High boilers | 0.35 |

| | |
|---|---|
| n-Pentanal conversion (% of theory) | 97.7 |
| Selectivity for n-pentanoic acid (% of theory) | 99.3 |

Preparation of N-Heptanoic Acid

Comparative example 2

The liquid-phase oxidation of n-heptanal to n-heptanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 $\mu$m and was connected to the bubble column.

In each of the oxidations, 800.0 g of n-heptanal of the following composition determined by gas chromatography were employed:

0.62% low boilers
97.74% n-heptanal
0.10% n-heptanoic acid
1.54% high boilers

The results after oxidation at a constant 50° C. for 6 hours were as follows:

| | |
|---|---|
| Weight of oxidation product (g) | 892.0 |
| GC analysis (%): | |
| Low boilers | 0.82 |
| n-Heptanal | 5.41 |
| n-Heptanoic acid | 91.80 |
| High boilers | 1.97 |
| n-Heptanal conversion (% of theory) | 93.8 |
| Selectivity for n-heptanoic acid (% of theory) | 98.9 |

Example 7

This test was carried out under the conditions of comparative example 2 with the difference that the starting aldehyde contained 4.98% by weight 2-methylhexanal in addition to 92.86% by weight n-heptanal (equivalent to a molar ratio of 100 to 5.36).

800.0 g of this mixture were employed in the oxidation.

The results after oxidation at a constant 50° C. for 6 hours were as follows:

| | |
|---|---|
| Weight of oxidation product (g) | 897.3 |
| GC analysis (%): | |
| Low boilers | 1.34 |
| 2-Methylhexanal | 0.19 |
| n-Heptanal | 4.21 |
| 2-Methylhexanoic acid | 4.48 |
| n-Heptanoic acid | 88.01 |
| High boilers | 1.77 |
| n-Heptanal conversion (% of theory) | 94.9 |
| Selectivity for n-heptanoic acid (% of theory) | 98.7 |

Example 8

This test was carried out under the conditions of comparative example 2 with the difference that the starting aldehyde contained 10.03% by weight 2-methylhexanal in addition to 87.81% by weight n-heptanal (equivalent to a molar ratio of 100 to 11.42).

800.0 g of this mixture were employed in the oxidation.

The results after oxidation at a constant 50° C. for 6 hours were as follows:

| | |
|---|---|
| Weight of oxidation product (g) | 899.7 |
| GC analysis (%): | |
| Low boilers | 1.65 |
| 2-Methylhexanal | 0.41 |
| n-Heptanal | 2.80 |
| 2-Methylhexanoic acid | 8.86 |
| n-Heptanoic acid | 84.28 |
| High boilers | 2.00 |
| n-Heptanal conversion (% of theory) | 96.4 |
| Selectivity for n-heptanoic acid (% of theory) | 98.6 |

Preparation of N-Nonanoic Acid

Comparative Example 3

The liquid-phase oxidation of n-nonanal to n-nonanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 $\mu$m and was connected to the bubble column.

In each of the oxidations, 800.0 g of n-nonanal of the following composition determined by gas chromatography were employed:

0.33% low boilers
0.05% 2-methyloctanal
99.56% n-nonanal
0.06% high boilers

The results after oxidation at a constant 60° C. for 6 hours were as follows:

| | |
|---|---|
| Weight of oxidation product (g) | 887.8 |
| GC analysis (%): | |
| Low boilers | 0.51 |
| n-Nonanal | 5.27 |
| 2-Methyloctanoic acid | 0.05 |
| n-Nonanoic acid | 93.32 |
| High boilers | 0.85 |
| n-Nonanal conversion (% of theory) | 94.2 |
| Selectivity for n-nonanoic acid (% of theory) | 98.8 |

Example 9

This test was carried out under the conditions of comparative example 3 with the difference that the starting aldehyde contained 5.09% by weight 2-methyloctanal in addition to 94.52% by weight n-nonanal (equivalent to a molar ratio of 100 to 5.39).

800.0 g of this mixture were employed in the oxidation.

The results after oxidation at a constant 60° C. for 6 hours were as follows:

| | |
|---|---|
| Weight of oxidation product (g) | 889.4 |
| GC analysis (%): | |
| Low boilers | 1.14 |
| 2-Methyloctanal | 0.08 |
| n-Nonanal | 3.39 |
| 2-Methyloctanoic acid | 4.45 |
| n-Nonanoic acid | 90.33 |
| High boilers | 0.61 |
| n-Nonanal conversion (% of theory) | 96.0 |
| Selectivity for n-nonanoic acid (% of theory) | 98.7 |

Example 10

This test was carried out under the conditions of comparative example 3 with the difference that the starting aldehyde contained 8.10% by weight 2-methyloctanal in addition to 91.30% by weight n-nonanal (equivalent to a molar ratio of 100 to 8.87).

800.0 g of this mixture were employed in the oxidation.

The results after oxidation at a constant 60° C. for 6 hours were as follows:

| | |
|---|---|
| Weight of oxidation product (g) | 889.8 |
| GC analysis (%): | |
| Low boilers | 1.56 |
| 2-Methyloctanal | 0.11 |
| n-Nonanal | 2.98 |
| 2-Methyloctanoic acid | 6.99 |
| n-Nonanoic acid | 87.73 |
| High boilers | 0.63 |
| n-Nonanal conversion (% of theory) | 96.4 |
| Selectivity for n-nonanoic acid (% of theory) | 98.6 |

Example 11

This test was carried out under the conditions of comparative example 3 with the difference that the starting aldehyde contained 14.24% by weight 2-methyloctanal in addition to 85.14% by weight n-nonanal (equivalent to a molar ratio of 100 to 16.73).

800.0 g of this mixture were employed in the oxidation.

The results after oxidation at a constant 60° C. for 6 hours were as follows:

| | |
|---|---|
| Weight of oxidation product (g) | 889.2 |
| GC analysis (%): | |
| Low boilers | 2.71 |
| 2-Methyloctanal | 0.15 |
| n-Nonanal | 2.51 |
| 2-Methyloctanoic acid | 12.63 |
| n-Nonanoic acid | 81.02 |
| High boilers | 0.98 |
| n-Nonanal conversion (% of theory) | 96.8 |
| Selectivity for n-nonanoic acid (% of theory) | 97.2 |

What is claimed is:

1. A process for preparing straight-chain aliphatic carboxylic acids having 4 to 11 carbon atoms by oxidation of the corresponding straight-chain aldehydes with oxygen or oxygen-containing gas mixtures at 20 to 100° C., wherein the oxidation of the straight-chain aldehydes takes place in the presence of from 1 to 30 mol % of branched aldehydes per mol of straight-chain aldehydes.

2. The process as claimed in claim 1, wherein the oxidation of the straight-chain aldehydes takes place in the presence of from 2 to 15 mol %, of branched aldehyde per mol of straight-chain aldehyde.

3. The process as claimed in claim 1, wherein the branched aldehyde comprises 3 to 15, in carbon atoms.

4. The process of claim 1, wherein the side chain of the branched aldehyde is in the position α or β relative to the carbonyl group.

5. The process of claim 1, wherein the side chain is methyl or ethyl.

6. The process of claim 1, wherein the oxidation is carried out at temperatures in the range from 20 to 80° C.

7. The process of claim 1, wherein the oxidation is carried out under pressures in a range from atmospheric pressure to 1.0 MPa.

8. The process of claim 1, wherein the oxygen-containing gas mixtures have a content of up to 90% by volume of inert constituents.

9. The process of claim 2 wherein the amount of branched aldehyde is 5 to 10 mol %.

10. The process of claim 4 wherein the branched aldehyde comprises 4 to 11 carbon atoms.

11. The process of claim 6 wherein the oxidation is effected at 40 to 80°.

12. The process of claim 7 wherein the pressure is atmospheric pressure up to 0.8 MPa.

13. The process of claim 8 wherein the gas mixture contains 30 to 80% by volume of inert constituents.

* * * * *